United States Patent
Murali et al.

(10) Patent No.: US 6,740,665 B1
(45) Date of Patent: May 25, 2004

(54) TYROSINE KINASE INHIBITORS AND METHODS OF USING THE SAME

(76) Inventors: Ramachandran Murali, 41-6 Revere Rd., Drexel Hill, PA (US) 19026; Mark I. Greene, 300 Righters Mill Rd., Penn Valley, PA (US) 19072

( * ) Notice: Subject to any disclaimer, the term of this patent is extended or adjusted under 35 U.S.C. 154(b) by 0 days.

(21) Appl. No.: 09/913,128

(22) PCT Filed: Feb. 9, 2000

(86) PCT No.: PCT/US00/03341

§ 371 (c)(1),
(2), (4) Date: Mar. 12, 2002

(87) PCT Pub. No.: WO00/47205

PCT Pub. Date: Aug. 17, 2000

Related U.S. Application Data

(60) Provisional application No. 60/119,526, filed on Feb. 10, 1999.

(51) Int. Cl.[7] .......................... A61K 31/47; A61K 31/36
(52) U.S. Cl. .................. 514/312; 514/464; 514/466
(58) Field of Search ................ 514/466, 464, 514/44, 312

(56) References Cited

U.S. PATENT DOCUMENTS

| | | | |
|---|---|---|---|
| 6,197,754 B1 * | 3/2001 | Hung et al. ........... | 514/44 |
| 6,326,356 B1 * | 12/2001 | Hung et al. ........... | 514/44 |
| 6,395,712 B1 * | 5/2002 | Hung et al. ........... | 514/44 |

FOREIGN PATENT DOCUMENTS

| | | | |
|---|---|---|---|
| WO | WO 95/18606 | | 7/1995 |
| WO | WO97/35012 | * | 9/1997 |

OTHER PUBLICATIONS

Database HCAPLUS, Accession No. 1998:406637 Melzig et al., "Inhibition of lipopolysaccharide (LPS)–induced endothelial cytotoxicity by selected flavonoids", *Planta Med.*, 1998, 64:397–399.

Database HCAPLUS, Accession No. 1996:526603 Jiang et al., "Curcumin induces apoptosis in immortalized NIH 3T3 and malignant cancer cell lines", *Cancer Nutr.*, 1996, 26:111–120.

Database HCAPLUS, Accession No. 1995:231736 Kuo et al., "Reversion of the transformed phenotypes of v–H–ras NIH3T3 cells by flavonoids through attenuating the content of phosphotyrosine", *Cancer Lett.*, 1994, 87:91–97.

Database HCAPLUS, Accession No. 1995:209906 Sharma et al., "Screening of potential chemopreventive agents using biochemical markers of carcinogenesis", *Cancer Res.*, 1994, 54:5848–5855.

* cited by examiner

*Primary Examiner*—Vickie Kim
(74) *Attorney, Agent, or Firm*—Darby & Darby

(57) ABSTRACT

Tyrosine kinase inhibitors and pharmaceutical composition comprising the same are disclosed. Methods of treating mammals who have p185 tumors and methods of preventing p185 tumors in mammals at elevated risks of developing such tumors are disclosed. The methods comprise the step of administering effective amounts pharmaceutical compositions comprising a pharmaceutically acceptable carrier or diluent, and, a tyrosine kinase inhibitor to the mammal.

6 Claims, No Drawings

TYROSINE KINASE INHIBITORS AND METHODS OF USING THE SAME

This application is a 371 of PCT/US00/03341 filed Feb. 9, 2000 which claim benefit of No. 60/119526 filed Feb. 10, 1999.

FIELD OF THE INVENTION

The present invention is related to tyrosine kinase inhibitors, pharmaceutical compositions that comprise the same, and methods of using tyrosine kinase inhibitors to inhibit elevated tyrosine kinase activity associated with tumors that express p185. The present invention relates to methods of treating individuals who have cancer characterized by tumors with cells that express p185.

BACKGROUND OF THE INVENTION

The erbB family of receptors includes erbB1 (EGFR), erbB2 (p185), erbB3 and erbG4. Ullrich, et al. (1984) *Nature* 309,418–425, which is incorporated herein by reference, describes EGFR. Schechter, A. L., et al. (1984) *Nature* 312, 513–516, and Yamamoto, T., et al.(1986) *Nature* 319, 230–234, which are each incorporated herein by reference, describe p185neu/erbB2. Kraus, M. H., et al. (1989) *Proc. Natl. Acad. Sci. USA* 86, 9193–9197 which is incorporated herein by reference, describes erbB3 Plowman, G. D., (1993) *Proc. Natl. Acad. Sci. USA* 90, 1746–1750, which is incorporated herein by reference, describes erbB4.

The rat cellular protooncogene c-neu and its human counterpart c-erbB2 encode 185 kDa transmembrane glycoproteins termed p185. Tyrosine kinase (tk) activity has been linked to expression of the transforming phenotype of oncogenic p185 (Bargmann et al., *Proc. Natl. Acad. Sci. USA*, 1988, 85, 5394; and Stem et al., *Mol. Cell. Biol.*, 1988, 8, 3969, each of which is incorporated herein by reference). Oncogenic neu was initially identified in rat neuroglioblastomas (Schechter et al., *Nature*, 1984, 312, 513, which is incorporated herein by reference) and was found to be activated by a carcinogen-induced point mutation generating a single amino acid substitution, a Val to Glu substitution at position 664, in the transmembrane region of the transforming protein (Bargmann et al., Cell, 1986, 45, 649, which is incorporated herein by reference). This alteration results in constitutive activity of its intrinsic kinase and in malignant transformation of cells (Bargmann et al., *EMBO J.*, 1988, 7, 2043, which is incorporated herein by reference). The activation of the oncogenic p185 protein tyrosine kinase appears to be related to a shift in the molecular equilibrium from monomeric to dimeric forms (Weiner et al., *Nature*, 1989, 339, 230, which is incorporated herein by reference).

Overexpression of c-neu or c-erbB2 to levels 100-fold higher than normal (i.e., >$10^6$ receptors/cell) also results in the transformation of NIH3T3 cells (Chazin et al., *Oncogene*, 1992, 7, 1859; DiFiore et al., *Science*, 1987, 237, 178; and DiMarco et al., *Mol. Cell. Biol.*, 1990, 10, 3247, each of which is incorporated herein by reference). However, NIH3T3 cells or NR6 cells which express cellular p185 at the level of $10^5$ receptors/cell are not transformed (Hung et al., *Proc. Natl. Acad. Sci. USA*, 1989, 86, 2545; and Kokai et al., *Cell*, 1989, 58, 287, each of which is incorporated herein by reference), unless co-expressed with epidermal growth factor receptor (EGFR), a homologous tyrosine kinase (Kokai et al., *Cell*, 1989, 58, 287, which is incorporated herein by reference). Thus, cellular p185 and oncogenic p185 may both result in the transformation of cells.

Cellular p185 is highly homologous with EGFR (Schechter et al., *Nature*, 1984, 312, 513; and Yarnamoto et al., *Nature*, 1986, 319, 230, each of which is incorporated herein by reference) but nonetheless is distinct. Numerous studies indicate that EGFR and cellular p185 are able to interact (Stern et al., *Mol. Cell. Biol.*, 1988, 8, 3969; King et al., *EMBO J*, 1988, 7, 1647; Kokai et al., *Proc. Natl. Acad. Sci. USA*, 1988, 85, 5389; and Dougall et al., *J. Cell. Biochem.*, 1993, 53, 61; each of which is incorporated herein by reference). The intermolecular association of EGFR and cellular p185 appear to up-regulate EGFR function (Wada et al., *Cell*, 1990, 61, 1339, which is incorporated herein by reference). In addition, heterodimers which form active kinase complexes both in vivo and in vitro can be detected (Qian et al., *Proc. Natl Acad Sci. USA*. 1992, 89, 1330, which is incorporated herein by reference).

Similarly, p 185 interactions with other erbB family members have been reported (Carraway et al., *Cell* 1994, 78, 5–8; Alroy et al., *FEBS Lett.* 1997, 410, 83–86; Riese et al., *Mol. Cell. Biol.* 1995, 15, 5770–5776;Tzahar et al., *EMBO J*, 1997, 16, 4938–4950; Surden et al., *Neuron* 1997, 18, 847–855; Pirlcas-Kramarski et al., *Oncogene* 1997, 15, 2803–2815; each of which is incorporated herein by reference). Human p185 forms heterodimers with either erbB3 or erbB4 under physiologic conditions, primarily in cardiac muscle and the nervous system, particularly in development.

Cellular p185 proteins are found in adult secretory epithelial cells of the lung. salivary gland, breast, pancreas, ovary, gastrointestinal tract, and skin (Kokal et al., *Proc. Natl. Acad. Sci. USA*, 1987, 84, 8498; Mori et al., *Lab, Invest.*, 1989, 61, 93; and Press et al., *Oncogene*, 1990, 5, 953; each of which is incorporated herein by reference). Recent studies have found that the amplification of c-erbB2 occurs with high frequency in a number of human adenocarcinomas such as gastric (Akivama et al., *Science*, 1986, 232, 1644, which is incorporated herein by reference), lung (Kern et al., *Cancer Res.*, 1990, 50, 5184, which is incorporated herein by reference) and pancreatic adenocarcinomas (Williams et al., *Pathobiol.*, 1991, 59, 46, which is incorporated herein by reference). It has also been reported that increased c-erbB2 expression in a subset of breast and ovarian carcinomas is linked to a less optimistic clinical prognosis (Slamon et al., *Science*, 1987, 235, 177; and Slamon et al., *Science*, 1989, 244, 707, each of which is incorporated herein by reference). Heterodimeric association of EGFR and p185 has also been detected in human breast cancer cell lines, such as SK-Br-3 (Goldman et al., *Biochemistry*, 1990, 29, 11024, which is incorporated herein by reference), and transfected cells (Spivak-Kroizman et al., *J. Biol. Chem.*, 1992, 267, 8056, which is incorporated herein by reference). Additionally, cases of erbB2 and EGFR coexpression in cancers of the breast and prostate have been reported. In addition, heterodimeric association of p185 and erbB3 as well as heterodimeric association of p185 and erbB4 have also been detected in human cancers. Coexpression of erbB2 and erbB3 has been observed in human breast cancers. Coexpression of EGFR, erbB2, and erbB3 has been seen in prostate carcinoma.

As used herein, the term "p185" is meant to refer to the neu gene product and the erbB-2 gene product which are 185 kdalton receptor proteins as determined by carrying out electrophoresis on the glycoprotein and comparing its movement with marker proteins of known molecular weight. p185 has tyrosine kinases activity, forms homodimers with themselves and interacts with other members of the erbB family, such as erbB1 (epidermal growth factor receptor or EGFR), erbB3 and erbB4 to form heterodimers.

As used herein, the term "p185 tumors", "neu-associated cancer", "neu-associated tumors" and "p185-associated tumors" are used interchangably and are meant to refer to tumors with cells that express p185. A p185 tumor may contain cells that express p185 and, additionally, other members of the erbB family, such as erbB1 (EGFR), erbB3 and erbB4 to form heterodimers and EGFR. A p185 tumor may contain p185 homodimers and/or heterodimers including p185-EGFR heterodimers and/or p185-erbB3 heterodimers and/or p185-erbB4 heterodimers. Dimerization of p185 with other p185 molecules or other members of the p185 family is associated with elevated tyrosine kinase activity. Examples of p185 tumors include many human adenocarcinomas such as some breast, ovary, lung, pancreas, salivary gland, kidney, prostate adenocarcinomas and some neuroblastoma.

As used herein, the term "p185-mediated cellular transformation" is meant to refer to the cellular transformation that p185-associated tumor cell neoplasms undergo and whose transformed phenotype can be arrested and/or reversed by tyrosine kinase inhibitors.

As used herein, the term "high risk individual" is meant to refer to an individual who either a) has had a p185-associated tumor either removed or enter remission and who is therefore susceptible to a relapse or recurrence or b) has a genetic predisposition to develop p185 tumors. Individual who have had p185-associated tumor either removed or enter remission can be readily identified through personal medical history. Individuals who have a genetic predisposition to develop p185 tumors can be identified by those skilled in the art using various means such as by review of family medical history. As part of a treatment regimen for a high risk individual, the individual can be prophylactically treated against tumors that they have been diagnosed as having had in order to combat a recurrence or tumor development. Thus, once it is known that an individual has had a p185-associated cancer, the individual can be treated according to the present invention to prevent normal cells from transforming into tumor cells.

As used herein, the term "therapeutically effective amount" is meant to refer to an amount of a compound which produces a medicinal effect observed as reduction or reverse in tumorigenic phenotype of tumor cells in an individual when a therapeutically effective amount of a compound is administered to an individual who is susceptible to or suffering from p185 tumors. Therapeutically effective amounts are typically determined by the effect they have compared to the effect observed when a composition which includes no active ingredient is administered to a similarly situated individual.

As used herein, the term "prophylactically effective amount" is meant to refer to an amount of a compound which produces a medicinal effect observed as the prevention of non-transformed cells from becoming transformed in an individual when a prophylactically effective amount of a compound is administered to an individual who is susceptible to p185 tumors. Prophylactically effective amounts are typically determined by the effect they have compared to the effect observed when a composition which includes no active ingredient is administered to a similarly situated individual.

The present invention is useful to therapeutically treat an individual identified as suffering from p185-associated tumors in order to reverse the transformed phenotype of the tumor cells. The present invention is useful to prophylactically treat an individual who is predisposed to develop p185-associated tumors or who has had p185-associated tumors and is therefore susceptible to a relapse or recurrence.

The present invention provides novel compounds which have tyrosine kinase inhibitor activity and a formula selected from the group consisting of Formula 1, Formula 2, Formula 3 and Formula 4, as set forth in the section below entitled Formulae, or a pharmaceutically acceptable salt thereof.

The invention provides novel pharmaceutical compositions comprising tyrosine kinase inhibitors which can reduce the enhanced tyrosine kinase activity associated with p185 homodimers and p185-EGFR heterodimers, p185-erbB3 heterodimers and p185-erbB4 heterodimers. The tyrosine kinase inhibitors included in the pharmacuetical compositions of the present invention have a formula selected from the group consisting of Formula 1, Formula 2, Formula 3 and Formula 4, as set forth in the section below entitled Formulae, or a pharmaceutically acceptable salt thereof.

In some preferred embodiments, the tyrosine kinase inhibitor in the pharmacuetical compositions of the present invention has a formula of Formula 1 as set forth in the section below entitled Formulae. In some preferred embodiments, the tyrosine kinase inhibitor in the pharmacuetical compositions of the present invention has a formula of Formula 1 COMP11 ($F_1^1$), COMP12 ($F_2^1$), COMP13 ($F_3^1$), COMP14 ($F_4^1$), COMP15 ($F_5^1$), or COMP16 ($F_6^1$), as set forth in the section below entitled Formulae, or a pharmaceutically acceptable salt thereof.

In some preferred embodiments, the tyrosine kinase inhibitor in the pharmacuetical compositions of the present invention has a formula of Formula 2 as set forth in the section below entitled Formulae. In some preferred embodiments, the tyrosine kinase inhibitor in the pharmacuetical compositions of the present invention has a formula of Formula 2 COMP21 ($F_1^2$), COMP22 ($F_2^2$), COMP23 ($F_3^2$), COMP24 ($F_4^2$), or COMP 25($F_5^2$), as set forth in the section below entitled Formulae, or a pharmaceutically acceptable salt thereof.

In some preferred embodiments, the tyrosine kinase inhibitor in the pharmacuetical compositions of the present invention has a formula of Formula 3 as set forth in the section below entitled Formulae. In some preferred embodiments, the tyrosine kinase inhibitor in the pharmacuetical compositions of the present invention has a formula of Formula 3 COMP31 ($F_1^3$), COMP32 ($F_2^3$), COMP33 ($F_3^3$), or COMP34 ($F_4^3$), as set forth in the section below entitled Formulae. In some preferred embodiments, the tyrosine kinase inhibitor in the pharmacuetical compositions of the present invention has a formula of Formula 4 as set forth in the section below entitled Formulae. In some preferred embodiments, the tyrosine kinase inhibitor in the pharmacuetical compositions of the present invention has a formula of Formula 4 COMP41 ($F_1^4$), or COMP42 ($F_2^4$), as set forth in the section below entitled Formulae, or a pharmaceutically acceptable salt thereof.

The invention provides methods for treating mammals who have p185 tumors. A tyrosine inhibitor according to Formula 1, Formula 2, Formula 3 or Formula 4 is administered to the mammal in an amount effective to suppress tumor growth. The tyrosine kinase inhibitor reduces tyrosine kinase activity and thus suppresses tumor growth. In preferred embodiments, the tyrosine kinase inhibitor is COMP11($F_1^1$), COMP12 ($F_2^1$), COMP13 ($F_3^1$), COMP14 ($F_4^1$) COMP15 ($F_5^1$), COMP16 ($F_6^1$), COMP21 ($F_1^2$), COMP22 ($F_2^2$), COMP23 ($F_3^2$), COMP24 ($F_4^2$), COMP25 ($F_5^2$), COMP31 ($F_1^3$), COMP32 ($F_2^3$), COMP33 ($F_3^3$), COMP34 ($F_4^3$), COMP41 ($F_1^4$); or COMP42 ($F_2^4$), . . . as set forth in the section below entitled Formulae, or a pharmaceutically acceptable salt thereof.

The invention also provides novel therapeutic compositions for treating mammals who have p185 tumors. The methods comprise admininstering to such mammals a therapetucially effective amount of a tyrosine kinase inhibitor according to Formula 1, Formula 2, Formula 3 or Formula 4. In preferred embodiments, the tyrosine kinase inhibitor is COMP11 ($F_1^1$), COMP12 ($F_2^1$), COMP13 ($F_3^1$), COMP14 ($F_4^1$), COMP15 ($F_5^1$), COMP16 ($F_6^1$), COMP21 ($F_1^2$), COMP22 ($F_2^2$), COMP23 ($F_3^2$),COMP24 ($F_4^2$), COMP25 ($F_5^2$), COMP31 ($F_1^3$), COMP32 ($F_2^3$), COMP33 ($F_3^3$), COMP34 ($F_4^3$), COMP41 ($F_1^4$), or COMP42 ($F_2^4$), as set forth in the section below entitled Formulae, or a pharmaceutically acceptable salt thereof.

COMP11 ($F_1^1$), COMP 12 ($F_2^1$), COMP13 ($F_3^1$), COMP14 ($F_4^1$), COMP15 ($F_5^1$), COMP16 ($F_6^1$), COMP21 ($F_1^2$), COMP22 ($F_2^2$), COMP23 ($F_3^2$), COMP24 ($F_4^2$), COMP25 ($F_5^2$), COMP31 ($F_1^3$), COMP32 ($F_2^3$), COMP33 ($F_3^3$), COMP34 ($F_4^3$), COMP41 ($F_1^4$), or COMP42 ($F_2^4$), are each commercially available chemical entities as set forth in the section below entitled Sources.

In some embodiments, the method of the invention additionally includes the use of the tyrosine kinase inhibitors in combination with other methodologies to treat tumors. In some embodiments, the tyrosine kinase inhibitor is administered in conjunction with other chemotherapeutic agents. In some embodiments, the tyrosine kinase inhibitor is administered in conjunction with radiation therapy. In some embodiments, the tyrosine kinase inhibitor is administered in conjunction with other chemotherapeutic agents and radiation therapy.

In some embodiments of the invention, the expression of p 185 by cells of the tumor are identified prior to administration of the tyrosine kinase inhibitor. In some embodiments, samples of tumors may be removed such as biopsy samples and tested to identify the presence of p185 using p185-specific antibodies. The antibodies are preferably monoclonal antibodies. Those having ordinary skill in the art can routinely generate antibodies specific for p185 such as by the method in Harlow and Lane, eds., *Antibodies: A Laboratory, Manual*. Cold Spring Harbor Laboratory. Cold Spring Harbor. N.Y. 1988. A general method for the production of monoclonal antibodies comprises the steps of immunizing an animal such as a mouse or rat with an antigen to which monoclonal antibodies are desired. After allowing time for the immune system to generate lymphocytes capable of producing antibodies to the antigen, the animal is sacrificed and a suspension of spleen cells is prepared. The spleen cells are then fused with myeloma cells by contacting them in the presence of a fusion promoter such as polyethylene glycol. A percentage of the cells fuse to produce hybridomas. The earlier immunization of the animal from which the spleen cells were removed results in a number of lymphocytes which secrete antibody to the antigen of interest, a characteristic that is transferred genetically to the hybridoma during fusion of the spleen and myeloma cells. Hybridomas secreting monoclonal antibody having the desired specificity are then isolated using routine screening techniques. Antibodies against p185 are described in U.S. Pat. No. 5,677,171 issued Oct. 14, 1997, which is incorporated herein by reference, and U.S. Pat. No. 5,705,157 issued Jan. 6, 1998, which is incorporated herein by reference. Peptidomimetics of antibodies against p185 which bind to p185 and which can be used to identify the presence of p185 are described in U.S. Pat. No. 5,663,144 issued Sep. 2, 1997, which is incorporated herein by reference. Other methods for identifying tumors which express p185 may be designed routinely.

The pharmaceutical compositions comprising tyrosine kinase inhibitors of the present invention may be administered by any means that enables the active agent to reach the agent's site of action in the body of a mammal. Pharmaceutical compositions of the present invention may be administered by conventional routes of pharmaceutical administration. Pharmaceutical compositions may be administered parenterally, i.e., intratumor, intravenous, subcutaneous, intramuscular. Intravenous and intratumor administration are preferred routes. In some embodiments, the pharmaceutical compositions are administered orally. Pharmaceutical compositions are administered to the mammal for a length of time effective to reduce tumor size and as needed to maintain regression of the tumor.

Pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

Subsequent to initial administration, individuals may be boosted by readministration. In some preferred embodiments, multiple administrations are performed.

Pharmaceutical compositions may be formulated by one having ordinary skill in the art with compositions selected depending upon the chosen mode of administration. Suitable pharmaceutical carriers are described in *Remingion's Pharmaceutical Sciences*, A. Osol, a standard reference text in this field, which is incorporated herein by reference.

For parenteral administration, the compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride mannitol) and chemical stability (e.g. buffers and preservatives). The formulation is sterilized by commonly used techniques. In some embodiments, a parenteral composition suitable for administration by injection is prepared by dissolving 1.5% by weight of active ingredient in 0.9% sodium chloride solution.

According to some embodiments of the present invention, the composition is administered to tissue of an individual by topically or by lavage. The compounds may be formulated as a cream, ointment, salve, douche, suppository or solution for topical administration or irrigation. Formulations for such routes administration of pharmaceutical compositions are well known. Generally, additives for isotonicity can include sodium chloride, dextrose. mannitol, sorbitol and lactose.

In some cases, isotonic solutions such as phosphate buffered saline are used. Stabilizers include gelatin and albumin. In some embodiments, a vasoconstriction agent is added to the formulation. The pharmaceutical preparations according to the present invention are preferably provided sterile and pyrogen free.

A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

In some embodiments, the invention relates to methods of treating patients suffering from human adenocarcinomas which are p185-associated cancers such as gastric, lung and pancreatic adenocarcinomas and human breast and ovarian carcinomas as well as human breast and prostate cancer which are p185-associated cancer. In some embodiments, the invention relates to methods of preventing these p185-associated cancers in high risk individuals. In some embodiments, the invention relates to methods of preventing these p185-associated cancers in high risk individuals.

In some embodiments, the invention relates to methods of treating patients suffering from human epithelial malignancies erythroid leukemia, fibrosarcoma, angiosarcoma and melanoma. In some embodiments, the invention relates to methods of preventing these p185-associated cancers in high risk individuals.

According to some embodiments of the invention, the patient is treated with radiation or other chemotherapy in conjunction the administration of pharmaceutical compositions according to the invention. The use of multiple therapeutic approaches provides the patient with a broader based intervention.

According to some aspects of the present invention, in combination with administration of the composition that comprises the tyrosine kinase inhibitor, the individual is then administered a cytotoxic chemotherapeutic agent. In some embodiments, in combination with administration of the composition that comprises the tyrosine kinase inhibitor, the individual is exposed to chemotherapeutic agents and, additionally, to a therapeutic amount of gamma radiation. Chemotherapy approaches include administration of cytotoxic and or cytostatic agents. Chemotherapeutics are delivered according to standard protocols using standard agents, dosages and regimens. In some embodiments, the chemotherapeutic is selected from the group consisting of: cisplatin, doxirubicin, danurubicin, tamoxiphen, taxol, and methotrexate. Other examples of chemotherapeutics useful in the present invetion include, but are not limited to: cytosinarabinoside, etoposide, 5-4 fluorouracil, melphalan, chlorambucil, and other nitrogen mustards (e.g. cyclophosphamide), vindesine (and other vinca alkaloids), mitomycin and bleomycin. As a step in the method of the invention, chemotherapeutics may be administered to patients being treated or who have treated for tumors that express p185.

In some embodiments, radiotherapy follows administration of pharmaceutical compositions according to the invention. In some preferred embodiments, the radiation therapy using gamma radiation is provided following administration of compositions which convert radiation resistant tumors, radiation sensitive. According to aspects of the present invention, after administering the composition that comprises the tyrosine kinase inhibotir, the individual is then exposed to a therapeutic amount of gamma radiation. Gamma radiation is delivered according to standard radiotherapeutic protocols using standard dosages and regimens. Those skilled in the art can readily formulate an appropriate radiotherapeutic regimen. Carlos A Perez & Luther W Brady: *Principles and Practice of Radiation Oncology*, 2nd Ed. JB Lippincott Co, Phila., 1992, which is incorporated herein by reference describes radiation therapy protocols and parameters which can be used in the present invention. For GBMs (glioblastoma, the most malignant glial brain tumor). Simpson W. J. et al., Influence of location and extent of surgical resection on survival of patients with glioblastoma multiforms: Results of three consecutive Radiation Therapy Oncology Group (RTOG) clinical trials. *Int J Radiat Oncol Biol Phys* 26:239–244, 1993, which is incorporated herein by reference describes clinical protocols useful in the methods of the present invention. Similarly, for Borgelt et al., *The palliation of brain metastases: Final results of the first two studies of the Radiation Therapy Oncology Group Int J Radial Oncol Biol Phys* 6:1–9, 1980, which is incorporated herein by reference, describes clinical protocols useful in the methods of the present invention.

In some preferred embodiments, treatment with pharmaceutical compositions according to the invention is preceded by surgical intervention. According to some preferred embodiments, the present invention provides anti-cancer gene therapy treatment to treat residual, local disease, as a therapeutic adjuvant in combination with preexisting treatments. Delivery is local at the time of surgery, most likely after the resection of all gross disease. According to some embodiments of the invention, the pharmaceutical compositions are administered locally at the site of the tumor. In some embodiments, the pharmaceutical compositions are administered directly into the tumor cells and the tissue immediately surrounding the tumor.

In addition to treating mammals with p185 tumors, the present invention relates to methods of preventing tumors in any patient population identified as being susceptible to p185 tumors, it is particularly useful in high risk individuals who, for example, have a family history of cancer characterized by such tumors or those who show a genetic predisposition. Additionally, the present invention is particularly useful to prevent recurrence of such tumors in patients who have had such tumors removed by surgical resection or who have been diagnosed as having such cancer in remission.

Those having ordinary skill in the art can readily identify individuals who are susceptible to such tumors, particularly those individuals considered to be a high risk for whom the methods of the invention are particularly useful. Advancements in the understanding of genetics and developments in technology as well as epidemiology allow for the determination of probability and risk assessment an individual has for developing cancer. Using family health histories and/or genetic screening, it is possible to estimate the probability that a particular individual has for developing certain types of cancer. Those individuals that have been identified as being predisposed to developing a particular form of cancer can take only limited prophylactic steps towards reducing the risk of cancer. There is no currently available method or composition which can chemically intervene with the development of cancer and reduce the probability a high risk individual will develop cancer. Similarly, those individuals who have already developed cancer and who have been treated to remove the cancer or are otherwise in remission are particularly susceptible to relapse and reoccurrence.

In preferred embodiments, the methods of the present invention are useful to prophylactically and therapeutically treat humans.

The present invention is not intended to be limited by any theory. The present invention is further illustrated by the following examples, which are not intended to be limiting in any way.

EXAMPLE

Example 1 Tyrosine Kinase Activity

Membrane Purification

Cells were lysed by a combination of snap freeze-thawing and Dounce homogenization as described in Gaulton et al., *J Immunol.*, 1986, 7, 2470, which is incorporated herein by reference. The nuclear fraction was removed by centrifugation at 2000 xg for 5 minutes. The 2000 xg supernatant fraction was then recentrifuged at 25000 xg for 30 minutes at 4° C., and the 25000 xg supernatant was retained as the cytosol fraction. The pellet was redissolved in 1.5 ml of membrane buffer (40 mM NaCl, 0.1 mM EDTA, 20 mM HEPES (pH 6.8), 2 mM PMSF, and 5 mM Na pyrophosphate) then layered over a (20%–37%) sucrose solution in membrane buffer and centrifuged at 22000 rpm for 18 hours at 2° C by using a Beckrnan SW50.1 rotor. The membrane-rich interface was removed in 1 ml total volume, diluted with 10 ml of membrane buffer, and was recentrifuged at 40000 rpm for 60 minutes by using an SW40.1 rotor exactly as described in Zick et al., *Biochem. Biophys. Res. Commun.*, 1984, 119, 6, which is incorporated herein by reference. The resultant pellet containing purified membrane fragments, was redissolved in 100 $\mu$l of Kinase buffer (see below) per $10^7$ original cells. Membrane proteins were quantitated using a BioRad protein assay kit and stored at −80° C. until assay, Tyrosine Kinase Actvity In Membranes Membrane concentrations were determined by the method of Bradford as described in Gaulton et al., *J Immunol.*, 1986 7, 2470, which is incorporated herein by reference. Dilutions of membranes were incubated in quadruplicate in the presence or absence of synthetic polypeptide containing tyrosine as a specific indicator of tyrosine phosphorylation. Kinase reaction buffer, (50 $\mu$l of 0.1 M Hepes pH 7.3, 10 mM $MgCl_2$, 5 mM $MnCl^2$, 50 $\mu$M $Na_3VO_4$ were incubated in the presence of ATP (1 $\mu$Ci of gamma [$^{32}$P]ATP; Amersham) for 5 minutes at room temperature. Reactions were halted by adding 5 mM EDTA (final concentration) followed immediately by TCA immunoprecipitation onto glass fiber filters (Whatman GF/A). Filters were washed extensively with TCA followed by ether, air-dried, immersed in scintillation cocktail (Biofluor) and beta emissions determined. Quadruplicate wells assayed in the absence of tyrosine containing substrate were subtracted from tyrosine substrate containing wells.

Membrane proteins were incubated with the random polymer of glutamic acid-tyrosine (4:1) poly glu:tyr, PGT) as substrate for tyrosine phosphorylation as described in Zick et al., *Biochem. Biophys. Res. Commun.*, 1984, 119, 6, which is incorporated herein by reference. Briefly, membrane proteins were incubated in 50 $\mu$l of 10 mM HEPES pH 7.2 containing 10 mM $MgCl_2$, 100 $\mu$M $Na_3VO_4$ and 150 $\mu$M (10 $\mu$Ci) [$^{32}$P]ATP for 15 minutes at room temperature in the presence (specific) or absence (background) of poly glu:tyr substrate at 2.5 mg/ml. Reactions were stopped by the addition of EDTA to 50 mM final concentration and cold excess ATP and samples were spotted onto Whatman glass fiber filter paper. Filters were washed 3 times with ice cold 10% TCA containing 10 mM pyrophosphate and 1 mM ATP followed by once with acetate. Samples were then dried and counted in BioFlur (NEN). For immunoprecipitation of phosphotyrosine containing membrane proteins, 50 $\mu$g of purified membranes were incubated in kinase buffer as described above for 15 minutes. After labeling, samples were solubilized in Lysis buffer supplemented with 5 mM EDTA, precleared and immune precipitated with 2 $\mu$l ascites from MA-2G8A6 +protein A agarose. The MA-2G8 antibody specifically precipitates phosphotyrosine labeled polypeptides as described in Daniel et al., *Proc. Natl. Acad. Sci. USA*, 1985, 82, 2084, which is incorporated herein by reference.

SOURCES

| Compound | Source Company | Catalog Number |
| --- | --- | --- |
| 11 - $F_1^1$ | MAYBRIDGE | PD 00154 |
| 12 - $F_2^1$ | G&J RES | JS241 |
| 13 - $F_3^1$ | G&J | JS258 |
| 14 - $F_4^1$ | SALOR/ALDRICH | S11.804-4 |
| 15 - $F_5^1$ | SALOR/ALDRICH | S19,987-7 |
| 16 - $F_6^1$ | SALOR/ALDRICH | 23,838-4 |
| 21 - $F_1^2$ | APIN-NP | N069511 |
| 22 - $F_2^2$ | APIN-NP | N11493C |
| 23 - $F_3^2$ | KNOLL | 00105 |
| 24 - $F_4^2$ | FLUKA | 91950 |
| 25 - $F_5^2$ | SPECS | CIF6409 |
| 31 - $F_1^3$ | MAYBRIDGE | SEW 04598 |
| 32 - $F_2^3$ | MAYBRIDGE | SEW 04759 |
| 33 - $F_3^3$ | MAYBRIDGE | DP 01012 |
| 41 - $F_1^4$ | SALOR/ALDRICH | S25,931-4 |
| 42 - $F_2^4$ | G&J RESEARCH | JS572 |

List Of Company Addresses

Aldrich Chemical Company, Inc.
1001 West Saint Paul Avenue
Milwaukee, Wis. 53233
USA Fluka Chemie AG
Industriestrasse 25
P.O. Box 260
CH-9470 Buchs
SWITZERLAND Apin Chemical Ltd.
Unit 29D
Milton Park
Near Abingdon
Oxon OX 14 4RT
UNITED KINGDOM G&J Research Chemicals Ltd.
Fernworthy
Bridestowe
Okehampton, Devon, UK Knoll AG
Postfach 21 08 05
D-67008 Ludwigschafen GERMANY
Maybridge Chemical Company Ltd.
Trevillett
Tintagel
Cornwall PL34 0HW
UK
SPECS and BioSPECS B.V.
Fleminglaan 16
2289 CP Rijswijk
THE NETHERLANDS
Formulae
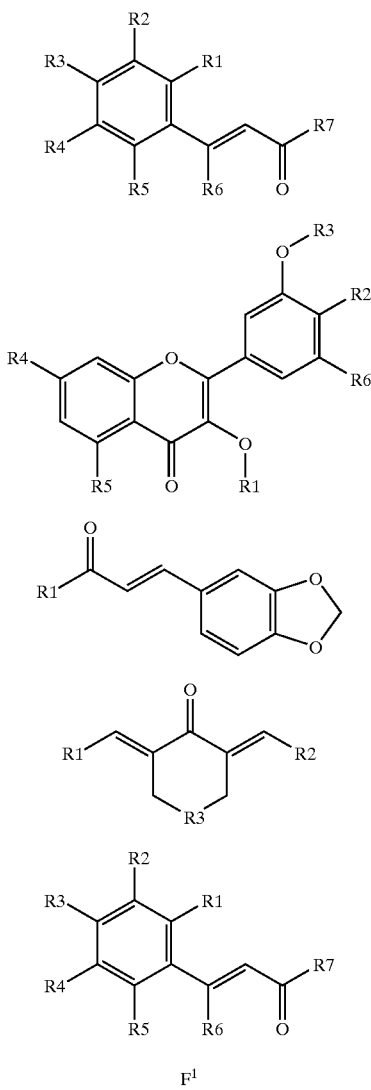
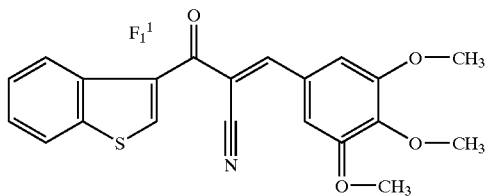
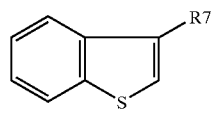
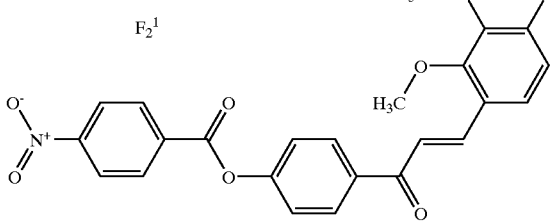
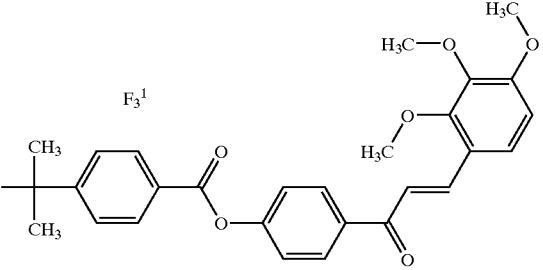
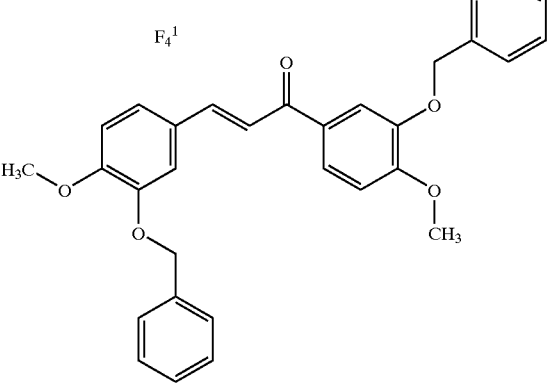

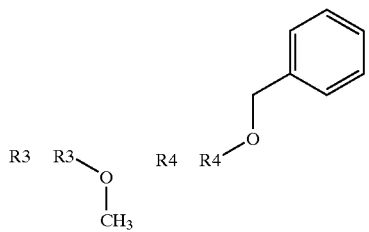
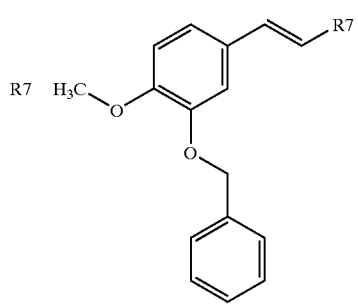
COMP 15
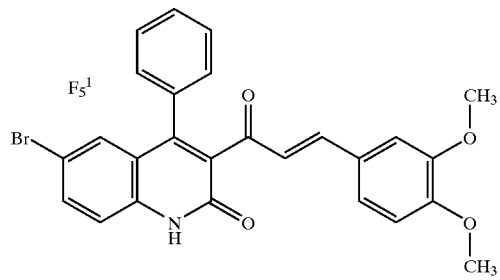
R3=R4 —O—CH₃
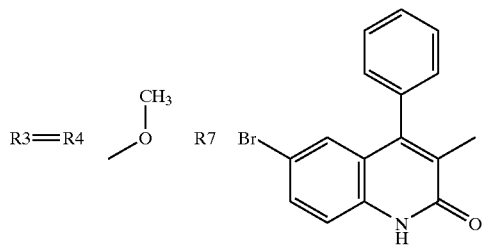
COMP16
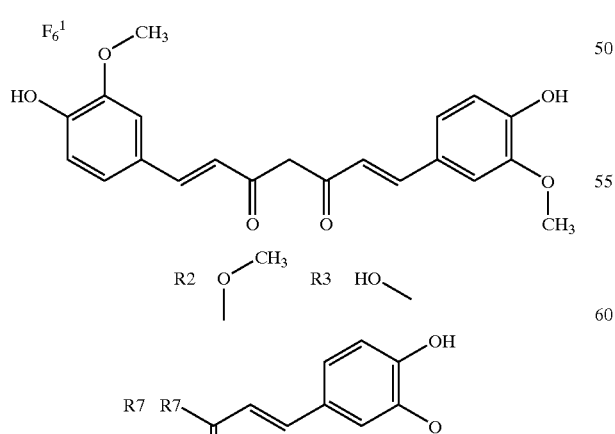
Formula 2
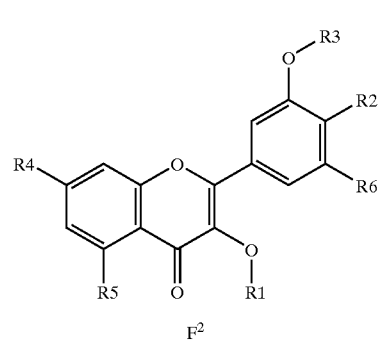
COMP21
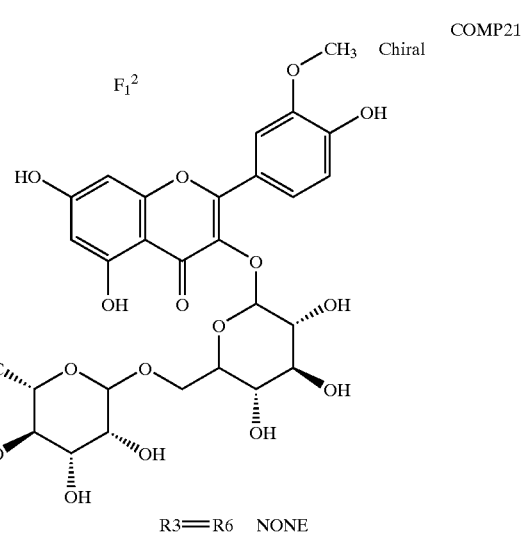
R3=R6 NONE
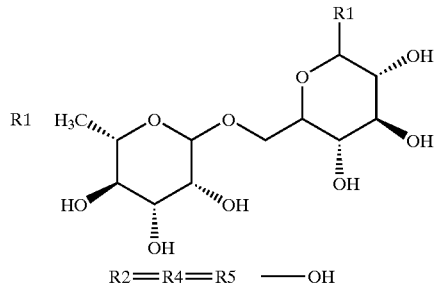
R2=R4=R5 —OH
COMP22
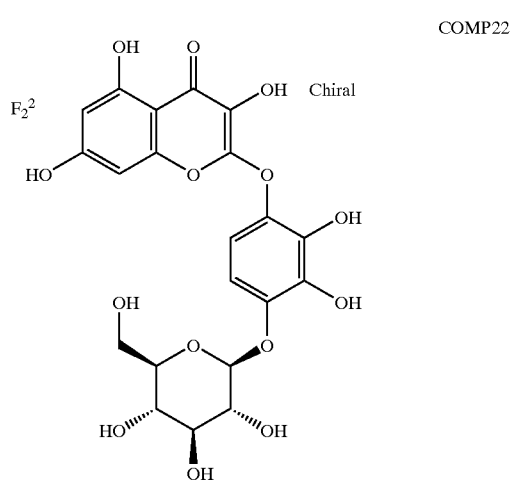

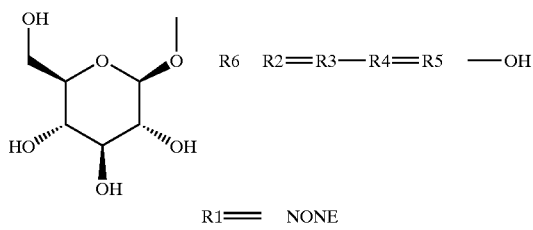
R6  R2=R3=R4=R5 —OH
R1= NONE
COMP23
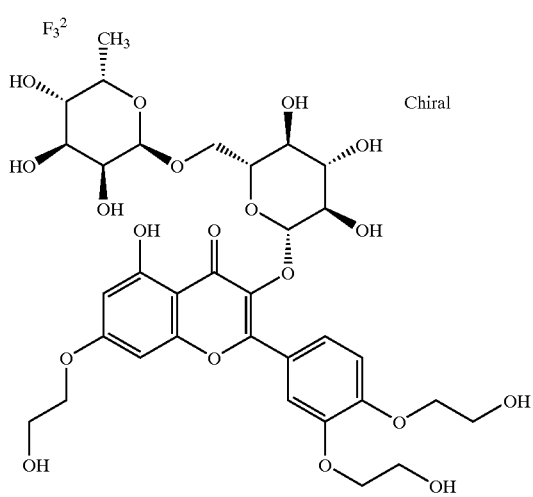
$F_3^2$
Chiral
COMP24
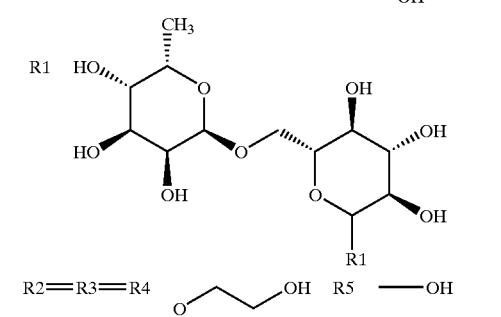
R2=R3=R4 —O—CH₂CH₂OH   R5 —OH
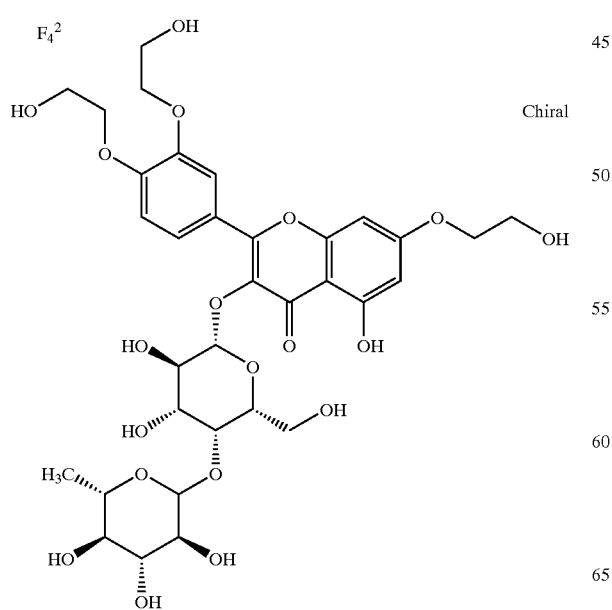
$F_4^2$
Chiral
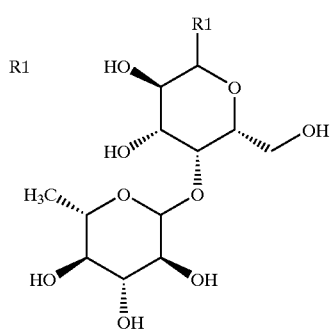
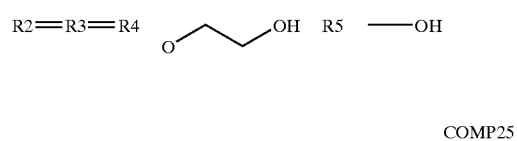
R2=R3=R4 —O—CH₂CH₂OH   R5 —OH
COMP25
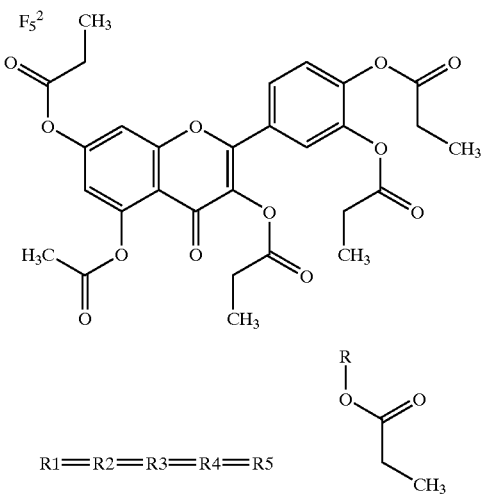
$F_5^2$
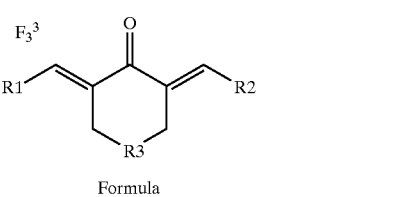
R1=R2=R3=R4=R5
$F_3^3$
Formula
COMP31
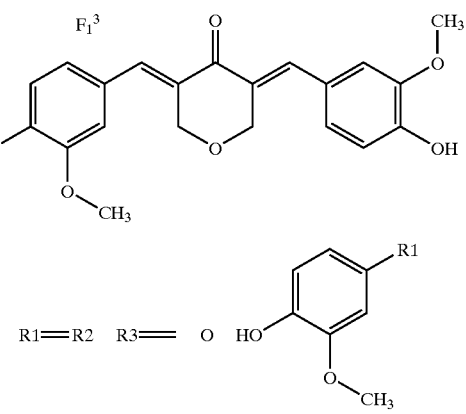
$F_1^3$
R1=R2   R3= O

COMP32

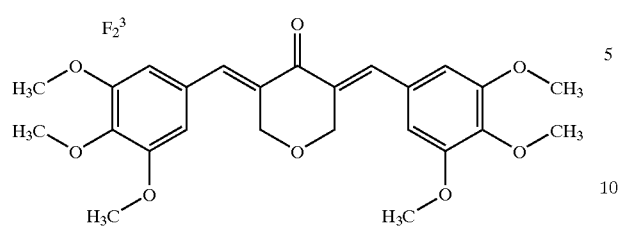

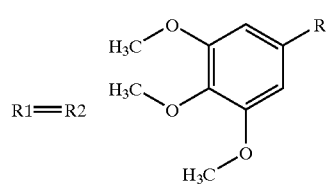

COMP33

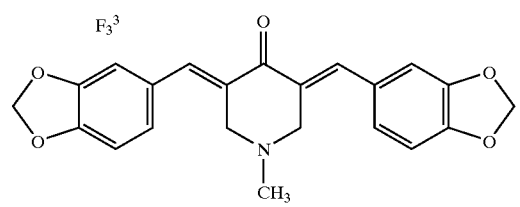

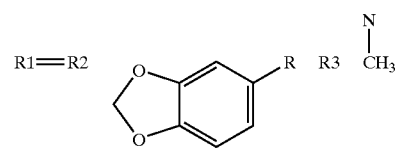

COMP41

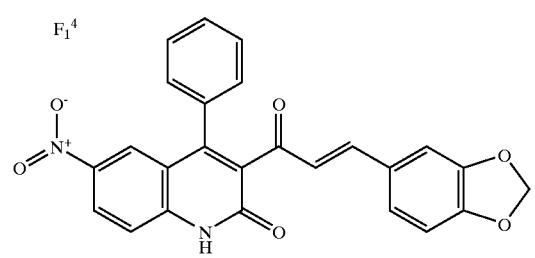

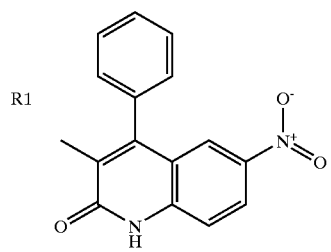

COMP42

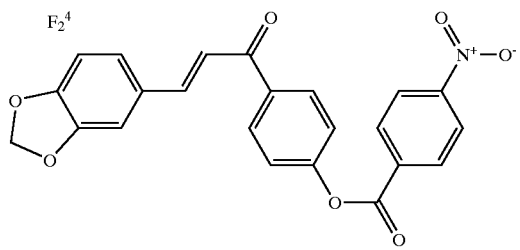

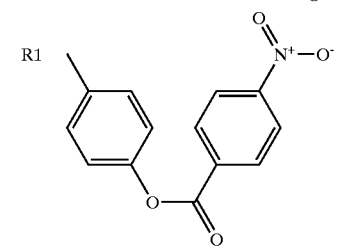

What is claimed is:

1. A method of treating a mammal who has a p185 tumor, said method comprising the step of administering to said mammal an amount of a pharmaceutical composition effective to reduce tumor growth, the pharmaceutical composition comprising:

(a) a compound having the structure

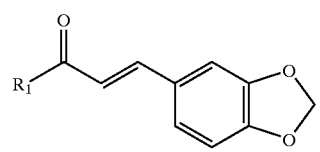

or a pharmaceutically acceptable salt thereof, wherein $R_1$ is

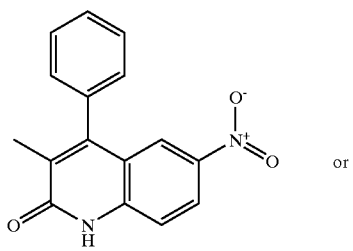

or

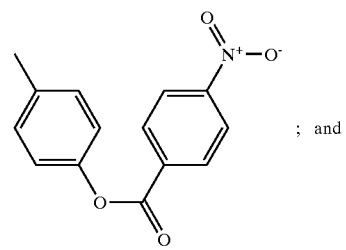

; and (b) a pharmaceutically acceptable carrier or diluent.

2. The method of claim 1 wherein said pharmaceutical composition is administered in combination with a therapeutically effective amount of anti-cancer radiation.

3. The method of claim 1 wherein said pharmaceutical composition is administered in combination with one or more other anti-tumor compositions.

4. The method of claim 3 wherein said other anti-tumor compositions are selected from the group consisting of: cisplatin, doxirubicin, danurubicin, tamoxiphen, taxol, methotrexate, cytosinarbinoside, etoposide, 5–4 fluorouracil, melphalan, chlorambucil, nitrogen mustards, vindesine, mitomycin and belomycin.

5. A method according to claim 1, wherein the pharmaceutical composition comprises a compound having the structure:

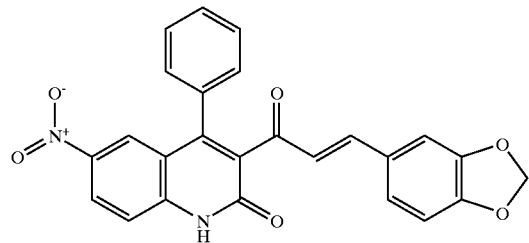

or a pharmaceutically acceptable salt thereof.

6. A method according to claim 1, wherein the pharmaceutical composition comprises a compound having the structure:

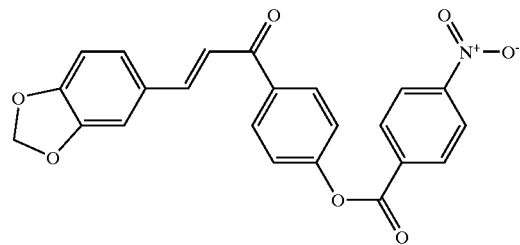

or a pharmaceutically acceptable salt thereof.

* * * * *